United States Patent
Bokil

(10) Patent No.: US 12,172,001 B2
(45) Date of Patent: *Dec. 24, 2024

(54) SELECTIVE ELECTRICAL MODULATION OF NEURAL POPULATIONS

(71) Applicant: Boston Scientific Neuromodulation Corporation, Valencia, CA (US)

(72) Inventor: Hemant Bokil, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 211 days.

This patent is subject to a terminal disclaimer.

(21) Appl. No.: 17/662,788

(22) Filed: May 10, 2022

(65) Prior Publication Data

US 2022/0265999 A1 Aug. 25, 2022

Related U.S. Application Data

(63) Continuation of application No. 16/850,747, filed on Apr. 16, 2020, now Pat. No. 11,338,129.

(60) Provisional application No. 62/835,324, filed on Apr. 17, 2019.

(51) Int. Cl.
*A61N 1/05* (2006.01)
*A61N 1/36* (2006.01)
*A61N 1/372* (2006.01)

(52) U.S. Cl.
CPC ....... *A61N 1/0534* (2013.01); *A61N 1/36067* (2013.01); *A61N 1/36146* (2013.01); *A61N 1/37229* (2013.01)

(58) Field of Classification Search
CPC .............. A61N 1/0534; A61N 1/36146; A61N 1/36067; A61N 1/37229; A61N 1/3615; A61N 1/36175
See application file for complete search history.

(56) References Cited

U.S. PATENT DOCUMENTS

| | | | |
|---|---|---|---|
| 5,752,979 A | 5/1998 | Benabid | |
| 6,819,956 B2 | 11/2004 | DiLorenzo | |
| 8,606,362 B2 | 12/2013 | He et al. | |
| 8,620,436 B2 | 12/2013 | Parramon et al. | |
| 9,610,443 B1 * | 4/2017 | Dean .................. | A61N 1/36034 |
| 9,776,003 B2 | 10/2017 | Alberts et al. | |
| 10,086,205 B2 | 10/2018 | Grill et al. | |

(Continued)

OTHER PUBLICATIONS

Fernandez-Suarez, Diana, et al., "Loss of Parvalbumin-Positive Neurons from the Globus Pallidus in Animal Models of Parkinson Disease," Journal of Neuropathology & Experimental Neurolgy, vol. 71, No. 11, Nov. 2012, pp. 973-982.

(Continued)

*Primary Examiner* — Brian T Gedeon
(74) *Attorney, Agent, or Firm* — Lewis & Reese, PLLC

(57) ABSTRACT

Methods of providing electrical neural modulation to a patient's brain are disclosed herein. The methods involve differentially modulating two or more target regions of the brain. For example, a first target region may be provided with an electrical neural modulation signal that activates that target region while a second target region is provided with an electrical neural modulation signal that suppresses or deactivates that target region. As the implantable pulse generators (IPGs) described herein include independent current sources, such differential modulation can be provided with a single IPG.

16 Claims, 6 Drawing Sheets

(56) References Cited

U.S. PATENT DOCUMENTS

| | | |
|---|---|---|
| 2007/0276450 A1 | 11/2007 | Meadows et al. |
| 2011/0160796 A1 | 6/2011 | Lane |
| 2011/0184487 A1 | 7/2011 | Alberts et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2015/0112409 A1 | 4/2015 | Hagedorn |
| 2015/0157861 A1 | 6/2015 | Aghassian |
| 2016/0023003 A1* | 1/2016 | Perryman .......... A61N 1/37205 607/116 |
| 2017/0072198 A1 | 3/2017 | Makous et al. |
| 2017/0106197 A1 | 4/2017 | Wechter et al. |
| 2017/0113048 A1* | 4/2017 | Giftakis ............. A61N 1/36139 |
| 2017/0120043 A1 | 5/2017 | John |
| 2017/0291030 A1* | 10/2017 | Shadmehr ................ A61N 1/20 |
| 2018/0071520 A1 | 3/2018 | Weerakoon et al. |
| 2018/0345022 A1 | 12/2018 | Steinke et al. |
| 2019/0083796 A1 | 3/2019 | Weerakoon et al. |

OTHER PUBLICATIONS

Mastro, Kevin J., et al., "Cell-Specific Pallidal Intervention Induces Long-Lasting Motor Recovery in Dopamine-Depleted Mice," Nature Neuroscience, 20, 2017, pp. 815-823.

Mastro, Kevin J., et al., "Transgenic Mouse Lines Subdivide External Segment of the Globus Pallidus (GPe) Neurons and Reveal Distinct GPe Output Pathways," The Journal of Neuroscience, Feb. 5, 2014, 34(6), pp. 2087-2099.

Lu et al., "Selective Extracellular Stimulation of Individual Neurons in Ganglia," J. Neural Eng., Sep. 2008, 5(3), pp. 287-309.

Popovych, Oleksandr V., et al., "Closed-Loop Deep Brain Stimulation by Pulsatile Delayed Feedback with Increased Gap Between Pulse Phases," Scientific Reports, 7:1033, Apr. 21, 2017, 14 pages.

Hernandez, Vivian M., et al., "Parvalbumin + Neurons and Npas1 + Neurons are Distinct Neuron Classes in the Mouse External Globus Pallidus," The Journal of Neuroscience, 35(34), Aug. 26, 2015, 18 pages.

\* cited by examiner

SELECTIVE ELECTRICAL MODULATION OF NEURAL POPULATIONS

CROSS REFERENCE TO RELATED APPLICATIONS

This is a continuation application of U.S. patent application Ser. No. 16/850,747, filed Apr. 16, 2020, which is a non-provisional application of U.S. Provisional Patent Application Ser. No. 62/835,324, filed Apr. 17, 2019. Priority is claimed to these applications, and they are incorporated herein by reference in their entireties.

FIELD OF THE INVENTION

The present invention relates to improved methods and systems for providing electrical modulation of distinct neural populations, as useful in Deep Brain Stimulation (DBS), for example.

INTRODUCTION

Implantable stimulation devices are devices that generate and deliver stimuli to nerves and nervous tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on Deep Brain Stimulation (DBS). However, the disclosed methods and systems may find applicability in any implantable stimulator system.

DBS has been used to treat a variety of neurological disorders, including Parkinson's disease (PD). Generally, such treatment involves placement of a DBS type lead into a targeted region of the brain through a burr hole drilled in the patient's skull, and the application of appropriate stimulation through the lead to the targeted region. In some cases, multiple brain regions may need to be electrically stimulated to treat one or more ailments associated with these brain regions. To this end, multiple stimulation leads are typically implanted adjacent the multiple brain regions. In particular, multiple burr holes are cut through the patient's cranium. However, the cutting of multiple burr holes and the introduction of the leads along multiple trajectories into the brain increases trauma and risk to the patient.

Stimulation of multiple brain regions with different sets of stimulation parameters may be optimum for treating the patient's symptoms. In many cases, if the same set of stimulation parameters is used to stimulate the different brain regions, either (1) one brain region may receive optimal therapy and the other brain region may receive poor therapy, or, (2) both brain regions may receive mediocre therapy. Thus, to maximize the therapeutic effects of DBS, each brain region may require different sets of stimulation parameters (i.e. different amplitudes, different durations, and/or frequencies, etc.).

One way that prior art DBS techniques attempt to stimulate several brain regions using different stimulation parameters is to implant multiple leads adjacent the different regions of the brain, and quickly cycling the stimulation through the brain regions with the different stimulation parameters. In some applications this effect may be unnoticeable. However, in some applications the effect of rapid cycling may produce a "helicopter effect" that may undesirably result in ineffective treatment and/or side-effects such as seizures.

Another way that prior art DBS techniques attempt to stimulate several brain regions using different stimulation parameters is to connect the multiple leads to multiple neurostimulators respectively programmed with different stimulation parameters. But this methodology has the obvious drawback that multiple neurostimulators must be surgically implanted in the patient, necessitating increased surgical intervention and the accompanying increased risk of complications.

Thus, there remains a need to provide an improved method for concurrently stimulating multiple brain regions with different sets of stimulation parameters.

SUMMARY

Methods of treating a patient are disclosed herein. According to some embodiments, the method comprises: identifying a first neural target for excitation in the brain, identifying a second neural target for suppression in the brain, exciting the first neural target using a first one or more stimulation waveforms comprising one or more pulses having a first polarity, and suppressing the second neural target using a second one or more stimulation waveforms comprising one or more pulses having a second polarity opposite of the first polarity. According to some embodiments, the first neural target is a first population of neural elements and the second neural target is a second population neural elements different than the first population of neural elements. According to some embodiments, the first one or more stimulation waveforms is applied at a first one or more electrodes implanted in a first region of the brain comprising the first population of neural elements. According to some embodiments, the second one or more stimulation waveforms is applied at a second one or more electrodes implanted in a second region of the brain comprising the second population of neural elements. According to some embodiments, the first one or more stimulation waveforms is applied at a first one or more electrodes implanted in a third region of the brain comprising a third population of neural elements having neural projections projecting to the first population of neural elements. According to some embodiments, the neural projections are excitatory neural projections and exciting the first population of neural elements comprises exciting the third population of neural elements using the first one or more stimulation waveforms. According to some embodiments, the neural projections are inhibitory neural projections and exciting the first population of neural elements comprises suppressing the third population of neural elements using the first one or more stimulation waveforms. According to some embodiments, the second one or more stimulation waveforms is applied at a second one or more electrodes implanted in a fourth region of the brain comprising a fourth population of neural elements comprising neural projections projecting to the second population of neural elements. According to some embodiments, the neural projections are excitatory neural projections and suppressing the second population of neural elements comprises suppressing the fourth population of neural elements using the second one or more stimulation waveforms. According to some embodiments, the neural projections are inhibitory neural projections and suppressing the second population of neural elements comprises exciting the fourth population of neural elements using the second one or more stimulation waveforms. According to some embodiments, the first one or more stimulation waveforms comprises cathodic pulses and wherein the second one or more stimulation waveforms comprises anodic pulses. According to some embodiments, the first one or more stimulation waveforms comprises coordinated reset stimulation waveforms. According to some embodiments, the first population of neural elements comprises PV-GPe neurons and the second population of neural elements comprises Lhx6-GPe neurons. According to some embodiments, the first region of the brain is the lateral region of the GPe and wherein the second region of the brain is the medial GPe.

Also disclosed herein is a method of treating a neural disorder in a patient, the method comprising: implanting an electrode lead in a patient's brain, wherein the electrode lead comprises a first one or more electrodes and a second one or more electrodes, wherein the electrode lead is implanted such that the first one or more electrodes are disposed in the patient's lateral GPe and the second one or more electrodes are disposed in the patient's medial GPe, at the first one or more electrodes, applying a first one or more stimulation waveforms comprising one or more pulses having a first polarity, and at the second one or more electrodes applying a second one or more stimulation waveforms comprising one or more pulses having a second polarity that is opposite of the first polarity. According to some embodiments, the first polarity is cathodic and the second polarity is anodic. According to some embodiments, the first stimulation waveform activates PV-GPe neurons and the second stimulation waveform suppresses Lhx6-GPe neurons.

DETAILED DESCRIPTION

Figure 1:
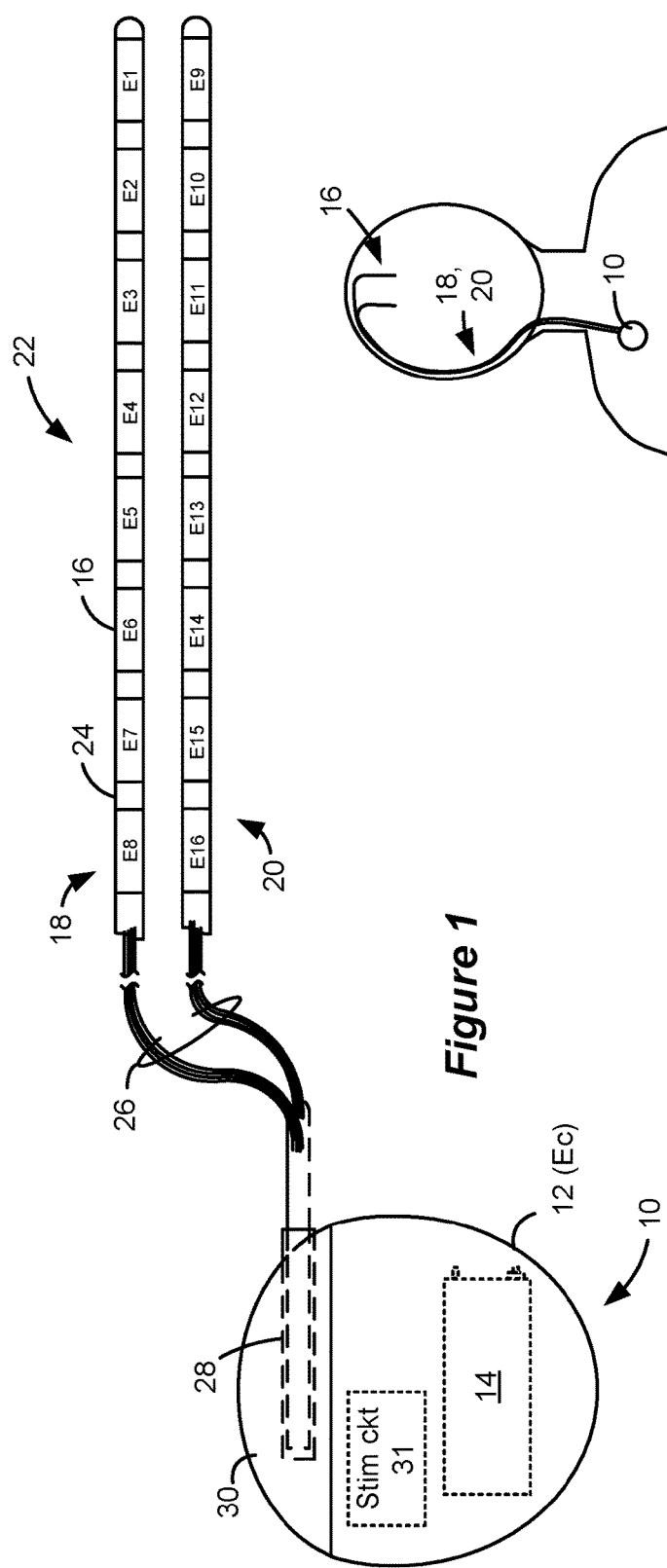
FIG. 1 shows an implantable pulse generator (IPG) with an electrode array.

As shown in FIG. 1, a DBS system typically includes an Implantable Pulse Generator (IPG) 10, which includes a biocompatible device case 12 formed of titanium for example. The case 12 typically holds the circuitry and battery 14 necessary for the IPG to function, although IPGs can also be powered via external energy and without a battery. The IPG case 12 also holds stimulation circuitry 31, which provides and controls electrical stimulation. As explained in more detail below, the case 12 may itself serve as an electrode (for example, as a counter-electrode) and, thus, the case 12 may be referred to as a case electrode ($E_c$).

Figure 2:
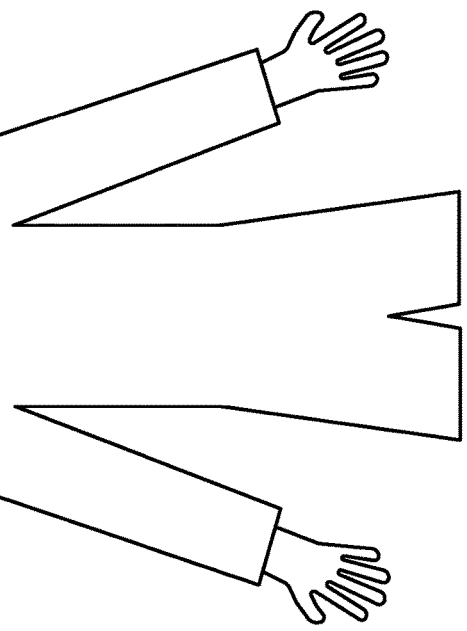
FIG. 2 shows implantation of the IPG in a patient in a Deep Brain Stimulation (DBS) application.

The IPG 10 is coupled to electrodes 16 via one or more electrode leads (two such leads 18 and 20 are shown), such that the electrodes 16 form an electrode array 22. The electrodes 16 are carried on a flexible body 24, which may also house individual signal wires 26 coupled to each electrode. In the illustrated embodiment, there are eight electrodes on electrode lead 18, labeled E1-E8, and eight electrodes on electrode lead 20, labeled E9-E16, although the number of leads and electrodes is application specific and therefore can vary. The proximal ends of leads 18 and 20 couple to the IPG 10 using lead connectors 28, which are fixed in a header material 30 comprising an epoxy for example. In a DBS application, as is useful in the treatment of Parkinson's disease for example, the IPG 10 is typically implanted under the patient's clavicle (collarbone), and the leads 18 and 20 are tunneled through the neck and between the skull and the scalp where the electrodes 16 are implanted through holes drilled in the skull in the left and right and side of the patient's brain, as shown in FIG. 2.

Figure 3:
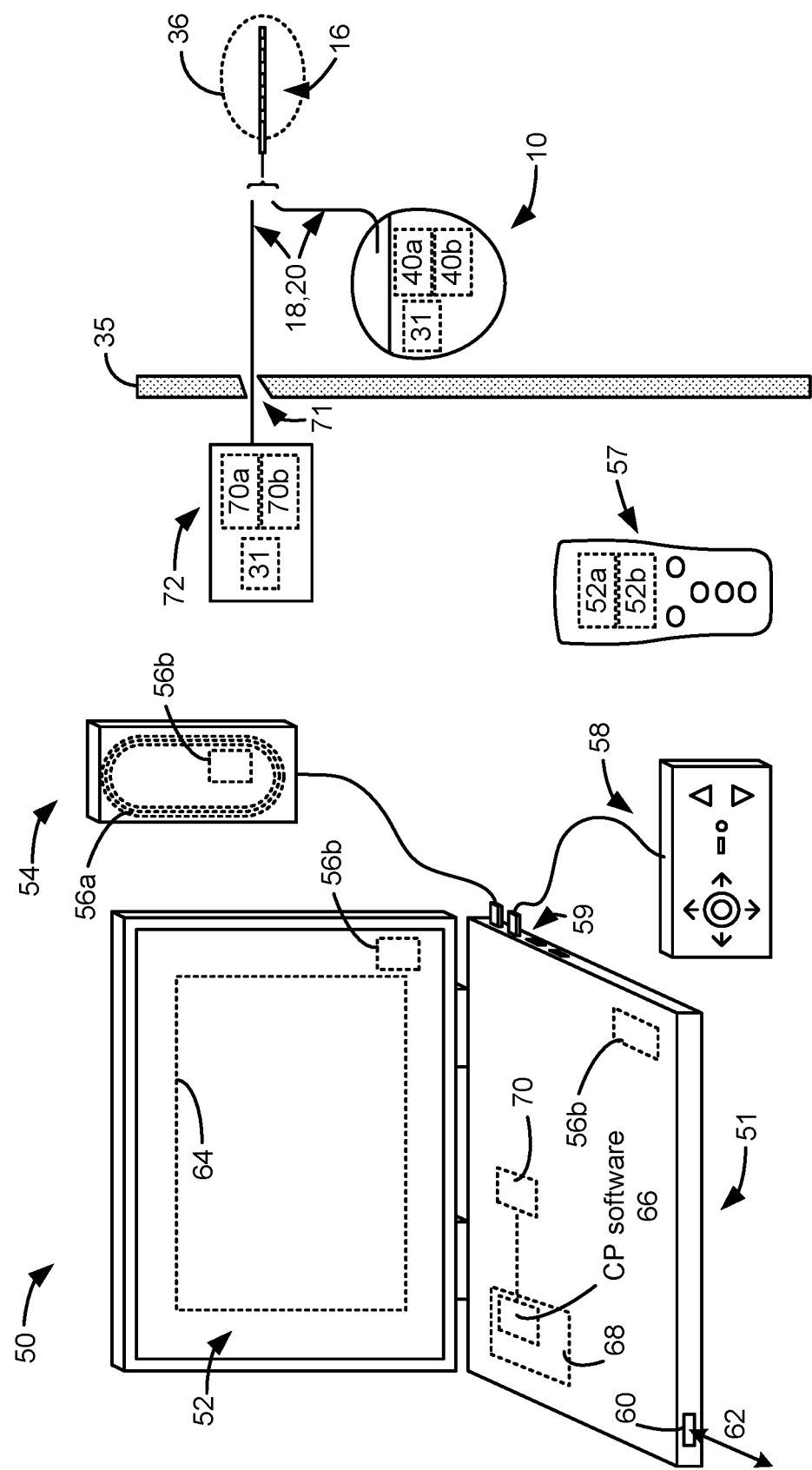
FIG. 3 shows implantation of one or more leads in target neural tissue, and connection of the lead(s) to an IPG or an External Trial Stimulation (ETS). External devices for programming the stimulation circuitry in the ETS or IPG, such as a clinician's programmer and a patient external controller, are also shown.

FIG. 3 shows an environment in which an implant patient can be "fitted," that is, where stimulation parameters for a patient can experimented with to hopefully find parameters that alleviate a patient's symptoms (e.g., tremor) while not introducing unwanted side effects. Stimulation is typically provided by pulses, and stimulation parameters typically include the amplitude of the pulses (whether current or voltage), the frequency and duration of the pulses, as well as the electrodes 16 selected to provide such stimulation, and whether such selected electrodes are to act as anodes (that source current to the tissue) or cathodes (that sink current from the tissue).

In FIG. 3, one or more of leads 18, 20 have been implanted within the patient's tissue 35 at a target location 36 as described above. The proximal ends of lead(s) 18, 20 can either be connected to an IPG 10 also implanted in the tissue 35, which IPG 10 includes stimulation circuitry 31 programmed to provide stimulation to the electrodes 16 consistent with the prescribed stimulation parameters. The proximal ends of lead(s) 18, 20 can also be at least temporarily connected to an External Trial Stimulation 72, which is typically used to provide stimulation during a trial phase after the lead(s) 18, 20 are implanted but before the IPG 10 is permanently implanted. The proximal ends of lead(s) 18, 20 exit an incision 71 in the patient's tissue 35 and are connected to the ETS 72. The ETS 72 mimics operation of the IPG 10 to provide stimulation pulses to the tissue, and so also includes programmable stimulation circuitry 31. The ETS 31 allows a clinician to experiment with the stimulation parameters and allows the patient to try stimulation for a trial period before the IPG 10 is permanently implanted.

Regardless whether trial stimulation is occurring via the ETS 72 or permanent stimulation is occurring via the IPG 10, a clinician programmer (CP) system 50 is shown that can be used by a clinician to adjust the stimulation parameters.

The CP system 50 includes a computing device 51, such as a desktop, laptop, or notebook computer, a tablet, a mobile smart phone, a Personal Data Assistant (PDA)-type mobile computing device, etc. (hereinafter "CP computer"). In FIG. 3, CP computer 51 comprises a laptop computer that includes typical computer user interface such as a screen 52, a mouse, a keyboard, speakers, a stylus, a printer, etc., not all of which are shown for convenience. Also shown in FIG. 3 are accessory devices for the CP system 50 that are usually specific to its operation as a stimulation controller, such as a communication wand 54, and a joystick 58, which can be connected to suitable ports on the CP computer 51, such as USB ports 59 for example. Joystick 58 is generally used as an input device to select various stimulation parameters (and thus may be redundant of other input devices to the CP), but is also particularly useful in steering currents between electrodes to arrive at an optimal stimulation program.

In operation, the clinician will use the user interface of the CP computer 51 to adjust the various stimulation parameters the ETS 72 or IPG 10 will provide, and such adjusted parameters can be wirelessly transmitted to the patient. Such wireless transmission can occur in different ways. The antenna used in the CP system 50 to communicate with the ETS 72 or IPG 10 can depend on the data telemetry antenna included in those devices. If the patient's ETS 72 or IPG 10 includes a coil antenna 70a or 40a, the wand 54 can likewise include a coil antenna 56a to establish communication over a near-field magnetic induction link at small distances. In this instance, the wand 54 may be affixed in close proximity to the patient, such as by placing the wand 54 in a holster, belt, or necklace wearable by the patient and proximate to the patient's ETS 72 or IPG 10.

If the ETS 72 or IPG 10 includes a far-field RF antenna 70b or 40b with longer communication distance, the wand 54, the CP computer 51, or both, can likewise include a short-range RF antenna 56b to establish communication with the ETS 72 or IPG 10. (In this example, a CP wand 54 may not be necessary if the CP computer 51 has the necessary short-range RF antenna 56b). If the CP system 50 includes a short-range RF antenna 56b, such antenna can also be used to establish communication between the CP system 50 and other devices, and ultimately to larger communication networks such as the Internet. The CP system 50 can typically also communicate with such other networks via a wired link 62 provided at an Ethernet or network port 60 on the CP computer 51, or with other devices or networks using other wired connections (e.g., at USB ports 59). Far-field RF antennas 56b, 70b, and/or 40b may operation with well-known communication standards such as Bluetooth, WiFi, ZigBee, MICS, etc.

To program stimulation parameters, the clinician interfaces with a clinician programmer graphical user interface (CP GUI) 64 provided on the display 52 of the CP computer 51. As one skilled in the art understands, the CP GUI 64 can be rendered by execution of CP software 66 on the CP computer 51, which software may be stored in the CP computer's non-volatile memory 68. One skilled in the art will additionally recognize that execution of the CP software 66 in the CP computer 51 can be facilitated by control circuitry 70 such as a microprocessor, microcomputer, an FPGA, other digital logic structures, etc., which is capable of executing programs in a computing device. Such control circuitry 70 when executing the CP software 66 will in addition to rendering the CP GUI 64 enable communications with the ETS 72 or IPG 10 as explained earlier, so that the clinician can use the CP GUI 64 to program the stimulation parameters to the stimulation circuitry 31 in the patient's ETS 72 or IPG 10.

A hand-held, portable patient external controller 57 can also be used to adjust stimulation parameters, which may include one or both of a coil antenna 52a or an RF antenna 52b capable of communicating with the ETS 72 of IPG 10. Further details concerning an external controller 57 can be found in the above-referenced '038 Publication.

Figure 4A:
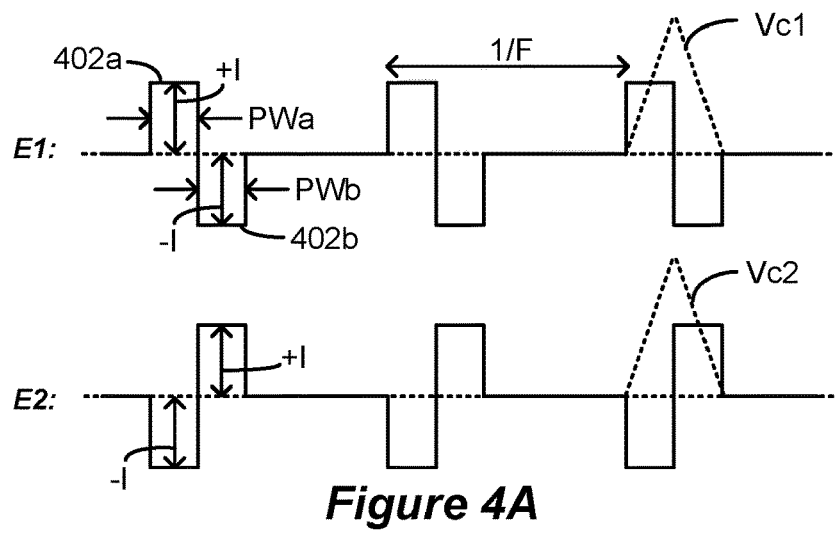
FIGS. 4A and 4B show an example of stimulation pulses producible by an IPG.

Stimulation in IPG 10 is typically provided by pulses, each of which may include a number of phases such as 402a and 402b, as shown in the example of FIG. 4A. The sequence of pulses may be referred to as a "pulse train." The variation of current (or voltage) as a function of time can be referred to as a "stimulation waveform." The stimulation waveform may be defined based on stimulation parameters. Stimulation parameters typically include amplitude (current I, although a voltage amplitude V can also be used); frequency (F); pulse width (PW) of the pulses or of its individual phases such as 402a and 402b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 31 in the IPG 10 can execute to provide therapeutic stimulation to a patient.

In the example of FIG. 4A, electrode E1 has been selected as an anode (during its first phase 402a), and thus provides pulses which source a positive current of amplitude +I to the tissue. Electrode E2 has been selected as a cathode (again during first phase 402a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. Moreover, the case 12 may act as an electrode Ec.

Figure 5:
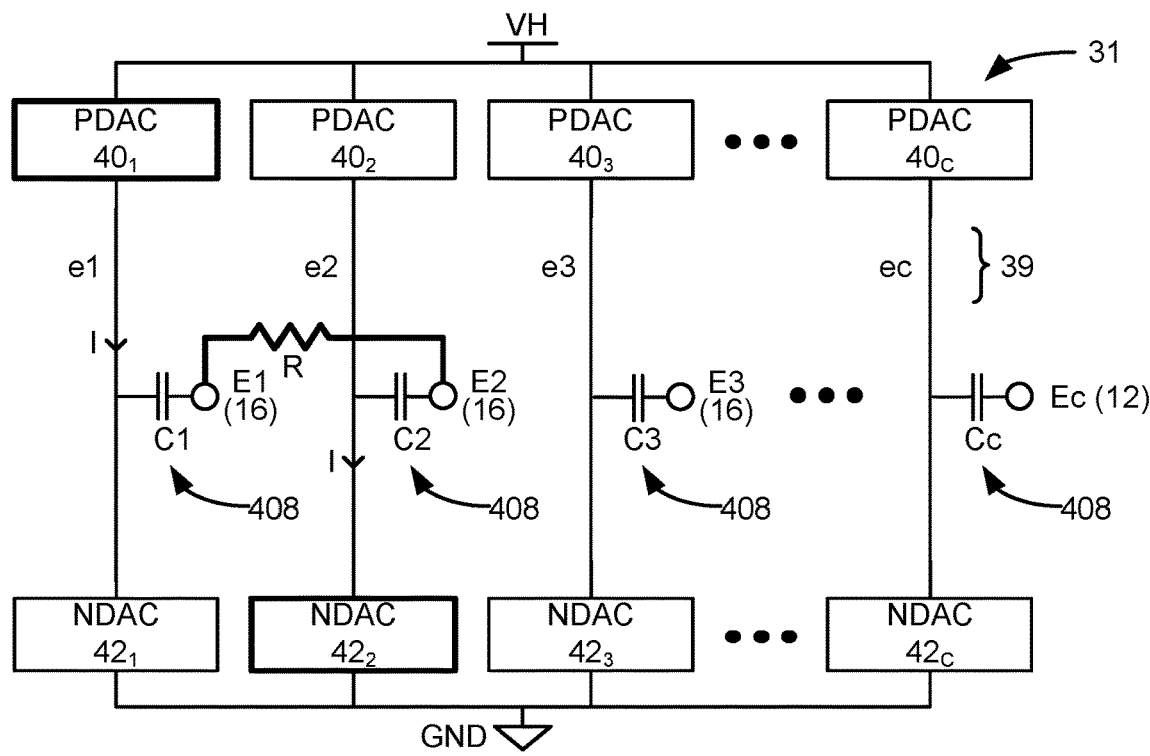
FIG. 5 shows stimulation circuitry useable in the IPG.

IPG 10 as mentioned includes stimulation circuitry 31 to form prescribed stimulation at a patient's tissue. FIG. 5 shows an example of stimulation circuitry 31, which includes one or more current source circuits 40$i$ and one or more current sink circuits 42$i$. The sources and sinks 40$i$ and 42$i$ can comprise Digital-to-Analog converters (DACs), and may be referred to as PDACs 40$i$ and NDACs 42$i$ in accordance with the Positive (sourced, anodic) and Negative (sunk, cathodic) currents they respectively issue. In the example shown, a NDAC/PDAC 40$i$/42$i$ pair is dedicated (hardwired) to a particular electrode node ei 409. Each electrode node ei 409 is connected to an electrode Ei 16 via a DC-blocking capacitor Ci 408, for the reasons explained below. The stimulation circuitry 31 in this example also supports selection of the conductive case 12 as an electrode (Ec 12), which case electrode is typically selected for monopolar stimulation. PDACs 40$i$ and NDACs 42$i$ can also comprise voltage sources.

Proper control of the PDACs 40$i$ and NDACs 42$i$ allows any of the electrodes 16 to act as anodes or cathodes to create a current through a patient's tissue, R, hopefully with good therapeutic effect. In the example shown, electrode E1 has been selected as an anode electrode to source current to the tissue R and E2 as a cathode electrode to sink current from the tissue R. Thus PDAC $40_1$ and NDAC $42_2$ are activated and digitally programmed to produce the desired current, I, with the correct timing (e.g., in accordance with the prescribed frequency F and pulse widths PWa and PWb). Power for the stimulation circuitry 31 is provided by a compliance voltage VH, as described in further detail in U.S. Patent Application Publication 2013/0289665. As shown, the compliance voltage may be coupled to the source circuitry (e.g., the PDAC(s)), while ground may be coupled to the sink circuitry (e.g., the NDAC(s)), such that the stimulation circuitry is coupled to and powered between the compliance voltage and ground. More than one anode electrode and more than one cathode electrode may be selected at one time, and thus current can flow through the tissue R between two or more of the electrodes 16.

Other stimulation circuitries 31 can also be used in the IPG 10. In an example not shown, a switching matrix can intervene between the one or more PDACs 40$i$ and the electrode nodes ei 409, and between the one or more NDACs 42$i$ and the electrode nodes. Switching matrices allows one or more of the PDACs or one or more of the NDACs to be connected to one or more anode electrode nodes at a given time. Various examples of stimulation circuitries can be found in U.S. Pat. Nos. 6,181,969, 8,606, 362, 8,620,436, U.S. Patent Publication 2018/0071520, and U.S. Patent Publication 2019/0083796.

Much of the stimulation circuitry 31 of FIG. 5, including the PDACs 40$i$ and NDACs 42$i$, the switch matrices (if present), and the electrode nodes ei 409 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas), circuitry for generating the compliance voltage VH, various measurement circuits, etc.

Also shown in FIG. 5 are DC-blocking capacitors Ci 408 placed in series in the electrode current paths between each of the electrode nodes ei 409 and the electrodes Ei 16 (including the case electrode Ec 12). The DC-blocking capacitors 408 act as a safety measure to prevent DC current injection into the patient, as could occur for example if there is a circuit fault in the stimulation circuitry 31, and also generally comprise part of the IPG's charge balancing mechanism. The DC-blocking capacitors 408 are typically provided off-chip (off of the ASIC(s)), and instead may be provided in or on a circuit board in the IPG 10 used to integrate its various components, as explained in U.S. Patent Application Publication 2015/0157861.

Figure 4B:
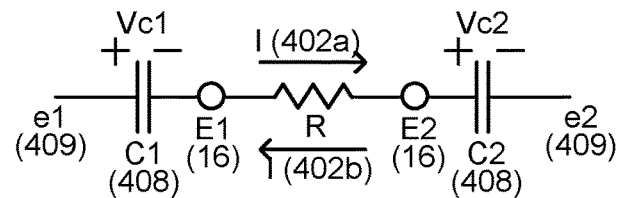

Referring again to FIG. 4A, the stimulation pulses as shown are biphasic, with each pulse comprising a first phase 402$a$ followed thereafter by a second phase 402$b$ of opposite polarity. Biphasic pulses are useful to actively recover any charge that might be stored on capacitive elements in the electrode current paths, such as on the DC-blocking capacitors 408. Charge recovery is shown with reference to both FIGS. 4A and 4B. During the first pulse phase 402$a$, charge will (primarily) build up across the DC-blockings capacitors C1 and C2 associated with the electrodes E1 and E2 used to produce the current, giving rise to voltages Vc1 and Vc2 (I=C*dV/dt). During the second pulse phase 402$b$, when the polarity of the current I is reversed at the selected electrodes E1 and E2, the stored charge on capacitors C1 and C2 is recovered, and thus voltages Vc1 and Vc2 hopefully return to 0V at the end the second pulse phase 402$b$.

To recover all charge by the end of the second pulse phase 402$b$ of each pulse (Vc1=Vc2=0V), the first and second phases 402$a$ and 402$b$ are charged balanced at each electrode, with the phases comprising an equal amount of charge but of the opposite polarity. In the example shown, such charge balancing is achieved by using the same pulse width (PWa=PWb) and the same amplitude (|+I|=|−I|) for each of the pulse phases 402$a$ and 402$b$. However, the pulse phases 402$a$ and 402$b$ may also be charged balance if the product of the amplitude and pulse widths of the two phases 402$a$ and 402$b$ are equal, as is known. It should be noted that, while biphasic pulses are illustrated in FIG. 4, monophasic pulses may be used and charge on the capacitors may be recovered passively.

In the illustrated embodiment, the IPG 10 can individually and independently control the magnitude of electrical current flowing through each of the electrodes. Significantly, the IPG 10 may be programmed to operate over multiple timing channels. The timing channel identifies which electrodes are selected to synchronously source or sink current to create an electric field in the tissue to be stimulated. The programming software in the CP 50 may be used to set stimulation parameters including electrode polarity, amplitude, pulse rate and pulse duration for the electrodes of a given timing channel, among other possible programmable features. The electrode combinations assigned to the respective timing channels may be completely different from each other or can have one or more common electrodes. Thus, multiple pulsed electrical waveforms can be concurrently delivered over multiple timing channels to any of the electrodes.

Traditionally, therapeutic neuromodulation has focused on activating or suppressing certain neural elements. For example, treatment of Parkinson's disease (PD) has utilized suppression of cell bodies in the subthalamic nucleus (STN), although the precise mechanism of action of the therapy remains a topic of debate. However, since the neurostimulation systems described herein utilize independently controllable current sources (i.e., PDACs 40 and NDACs 42) and multiple timing channels, more flexible treatment modalities are possible.

In some cases, the best therapy may be obtained by activating (i.e., exciting) some neural elements while deactivating (i.e., suppressing) other neural elements. One example is the selective electrical modulation of different areas of the external segment of the globus pallidus (GPe) for the treatment of motor dysfunction in movement disorders, such as dystonia and PD. The GPe is a central nucleus in the moto-suppressing indirect pathway, which receives inputs from the striatum, STN, and parafascicular nucleus of the thalamus (pf). The GPe has been implicated in the onset and maintenance of motor dysfunction in movement disorders. The activity of GPe neurons in patients suffering from PD is reduced and the synchronization of GPe neurons is thought to contribute to pathological oscillations.

The GPe comprises distinct neuronal populations, including populations of parvalbumin-expressing (PV-GPe) neuronal elements and populations of Lim homeobox 6 (Lhx6-GPe) neuronal elements, which do not express PV. The PV-GPe neurons are concentrated in the lateral region of the GPe whereas the Lhx6-PV neurons are concentrated in the medial GPe.

The densities of the projections that the PV-GPe and Lhx6-GPe neuronal populations make into other brain regions differ, suggesting that the two neural populations participate in different circuits in the brain and contribute to different aspects of motor function and dysfunction. Specifically, the striatum and substantia nigra compacta (SNc) are more densely innervated by Lhx6-GPe neurons, whereas the STN and pf are more densely innervated by PV-GPe neurons.

The SNc contains most of the dopamine neurons that innervate the dorsal striatum and the GPe. Dopamine release from the SNc is involved in motor aspects of basal ganglia function. Thus, Lhx6-GPe neurons play an influential role in movement. Because of their projections to striatal interneurons and SNc dopamine neurons, Lhx6-GPe neurons can be targeted to regulate striatal output and influence the balance of direct and indirect pathway activity to determine levels of motor output.

Axonal projections of PV-GPe neurons to the STN are stronger than those of Lhx6-GPe neurons, especially in the inner region of the nucleus, which is strongly innervated by PV-GPe neurons but not by Lhx6-GPe neurons. The GPe and STN form a reciprocally connected network that is implicated in pathological oscillations in PD. Thus, therapy targeting PV-GPe with their denser neuronal projections to the STN may be implicated in the prevention of such pathological oscillations. Moreover, the PV-GPe neurons strongly project into the pf, which plays a role in attention and behavioral flexibility. The dense projections of PV-GPe neurons to the pf suggest that they are an important component of non-motor output pathways of the GPe. The pf plays a role in motor control and DBS in the pf has been particularly effective at alleviating tremors in patients with movement disorders. Thus, the PV-GPe neurons can be targeted by therapies directed to disrupting the generation of pathological oscillations and tremor in PD.

The PV-GPe and Lhx6-GPe neuronal populations also have different electrophysiological properties. PV-GPe neurons have narrower action potentials and can sustain higher maximum firing rates than Lhx6-GPe neurons, and are thus tuned to respond to rapid, high-frequency inputs. As a consequence, stimulation parameters may be adjusted to selectively target and affect PV-GPe or Lhx6-GPe neuronal populations.

Because the PV-GPe and Lhx6-GPe neural populations differ in their function and electrophysiological properties, the two neural populations can be differentially targeted for neuromodulation. For example, an electrode lead (such as lead 18 in FIG. 1) can be implanted in a patient's brain such that a first one or more electrodes are located proximate to the lateral region of the GPe, which is concentrated in PV-GPe neurons and a second one or more electrodes are located proximate to the medial region of the GPe, which is concentrated in Lhx6-PV neurons. The IPG 10 is used to provide neuromodulating waveforms to the two regions of the GPe. As the IPG 10 comprises independently controllable current sources (i.e., PDACs 40 and NDACs 42) and multiple timing channels, different waveforms can be provided to the two regions.

For example, according to one embodiment, a first one or more waveforms can be provided to the PV-GPe neurons using the first one or more electrodes, wherein the first one or more waveforms stimulate (i.e., excite) the PV-GPe cells. Likewise, a second one or more waveforms can be provided to the Lhx6-GPe neurons using the second one or more electrodes, wherein the second one or more waveforms deactivate or suppress the Lhx6-GPe neurons.

Figure 6:
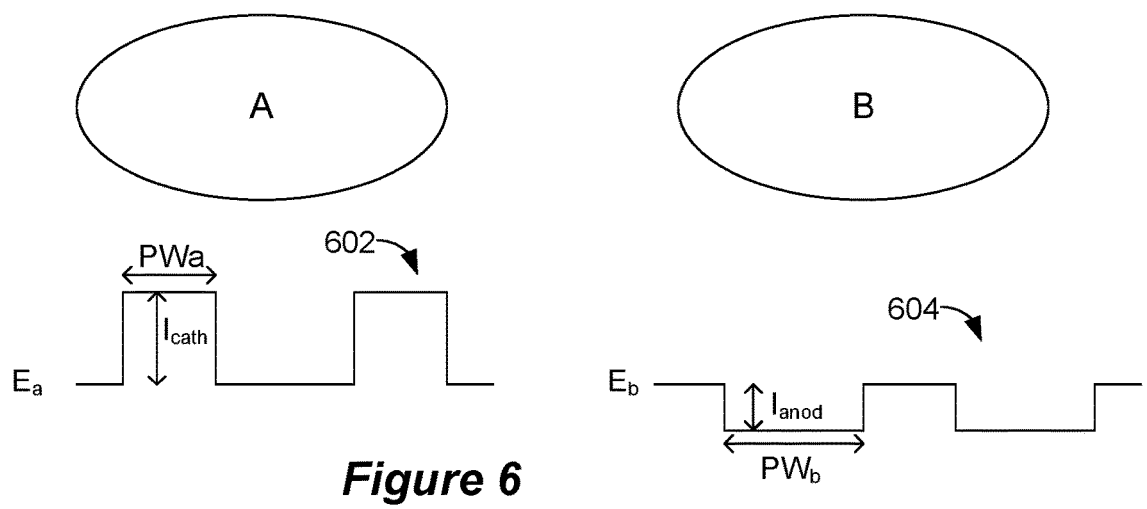
FIG. 6 shows an example of applying different stimulation waveforms to two neural targets.

More generally, the present disclosure provides techniques for activating certain neural elements while deactivating or suppressing certain other neural elements. FIG. 6 illustrates an embodiment, wherein the goal is to activate a first neural population A comprising A neurons and to suppress a second neural population B comprising B neurons. For example, the A neurons may be PV-GPe neurons and the B neurons may be Lhx6-GPe neurons. A first electrode Ea is placed in a region of neural anatomy with contains a majority of type A neurons and a second electrode Eb is placed in a region containing a majority of type B neurons. A stimulation waveform 602 (i.e., a pulse train) is applied at the electrode Ea and a different stimulation waveform (pulse train) 604 is applied at electrode Eb. In the illustrated example, the waveform 602 uses a cathodic pulse with an intensity $I_{cath}$ to excite the A neurons. The waveform 602 has a pulse width PWa. The waveform 604 uses an anodic intensity $I_{anod}$ to hyperpolarize the membranes of the B neurons, thereby reducing the firing of the neurons. The waveform 604 has a pulse width PWb. The cathodic and anodic waveforms can be interleaved or otherwise separated in time. The pulse patterns need not have the same pulse parameters. For example, in the illustrated example the hyperpolarizing waveform 604 is "long and low," i.e., it has a lower amplitude and a longer pulse width, whereas the cathodic waveform 602 is can use a typical DBS pulse. It should be noted that while monophasic pulses are illustrated in FIG. 6, generally any type of waveform can be applied at either of the electrodes Ea and/or Eb. For example, biphasic pulses may be applied as well as waveforms having more complicated pulse shapes, for example, having pre-pulse components, interphase components, and the like, as is known in the art.

Figure 7:
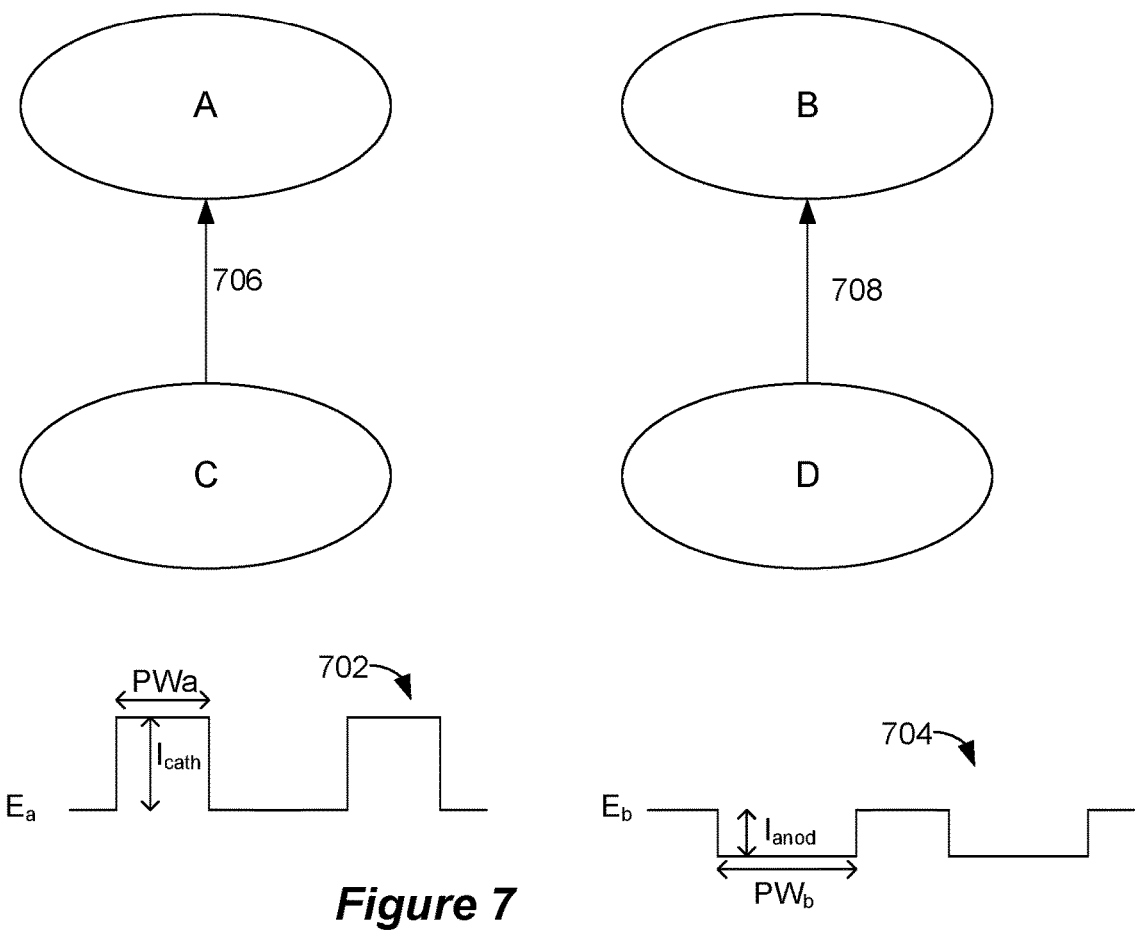
FIG. 7 shows an example of indirectly neuromodulating ultimate neural targets by applying stimulation waveforms to remote neural targets that project into the ultimate neural targets.

While the activity of target neural populations can be modulated directly, target neural populations can also be modulated indirectly by stimulating or suppressing other remote neural populations that project to the target neural population. For example, FIG. 7 illustrates an embodiment wherein neural elements C project to a region of neural anatomy comprising elements A, and neural elements D project to a region of neural anatomy comprising elements B. The neural projections are labeled as 706 and 708, respectively. Electrodes implanted proximate to neural elements C and D can be used to indirectly modulate neural targets A and B, respectively. The effect on the ultimate neural targets (i.e., A and/or B) of applying waveforms to the remote neural targets (i.e., C and/or D) will depend on whether the neural projections 706/708 are excitatory or inhibitory. If the projections are excitatory, then excitation of the remote neural target population will result in excitation of the ultimate target neural population, whereas suppression of the remote neural target population will result in suppression of the ultimate target population. If the projections are inhibitory, then excitation of the remote target neural population will result in inhibition of the ultimate target neural population, whereas suppression of the remote target neural population will result in excitation of the ultimate target neural population.

Thus, aspects of the disclosure provide methodologies for modulating one or more ultimate target neural populations by identifying one or more remote target neural populations that project into the ultimate target neural population(s) and determining if the neural projections are excitatory or inhibitory. Such identification may be based on imaging, histology, staining, or the like. The nature of the projections may be determined based on sensing/recording neural signals evoked during the modulation of the remote target neural populations. For example, evoked compound action potentials (ECAPs) may be sensed from axonal projections of ultimate target populations and firing rates may be sensed from the cell bodies. Referring to FIG. 7, assume that the projections 706 and 708 are both excitatory projections. When the remote target neural population C is excited using excitatory waveform 702 firing of the ultimate target neural population A will increase. Sensing of ECAPs associated with the firing of the ultimate target neural population A can be used to confirm the excitatory nature of the neural projection 706.

Figure 8:
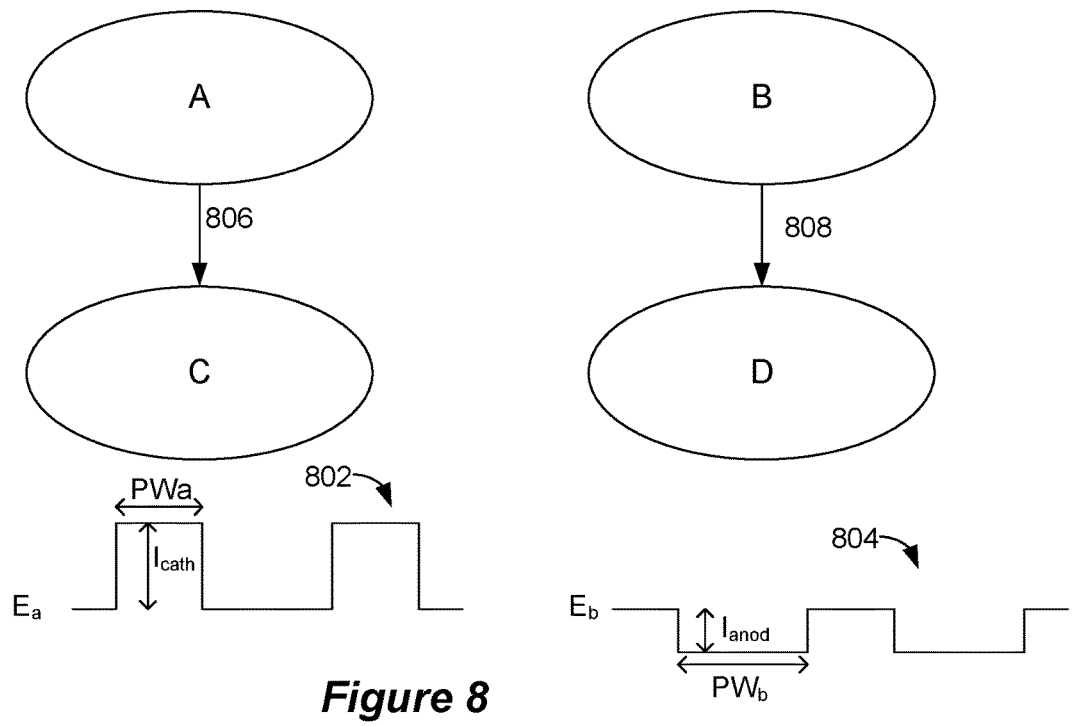
FIG. 8 shows an example of indirectly modulating the activity of ultimate neural targets by applying stimulation waveforms to remote neural targets to which the ultimate neural targets project.

Referring to FIG. 8, assume that A is a neural population, the activity of which is to be enhanced and B is a neural population, the activity of which is to be inhibited. Assume further that effect of A and B on the symptoms is mediated through neural populations C and D, respectively, that are neurologically "downstream" of the ultimate target neural populations A and B. In other words, assume that the ultimate target neural population A projects to the remote target neural population C via neural projections 806 and that the ultimate target neural population B projects to the remote target neural population D via neural projections 808 and that the effect of A on the brain network implicated in the symptoms being treated are mediated through C, and the effect of B on the brain network are mediated through D. Again, the neural projections 806/808 can be excitatory or inhibitory, as discussed above. Assume that in the embodiment illustrated in FIG. 8 the neural projections 806 and 808 are both excitatory projections. Since A activates C, the physiological activity resulting from the firing of the neural population A can be enhanced by applying a stimulating waveform 802 directly to the remote target neural population C. Likewise, the physiological activity resulting from the firing of the neural population B can be suppressed by applying an inhibitory waveform 804 directly to the remote target neural population D. Again, if the neural projections are inhibitory, then suppressing C has the same effect on the network as activating A, etc.

Figure 9:
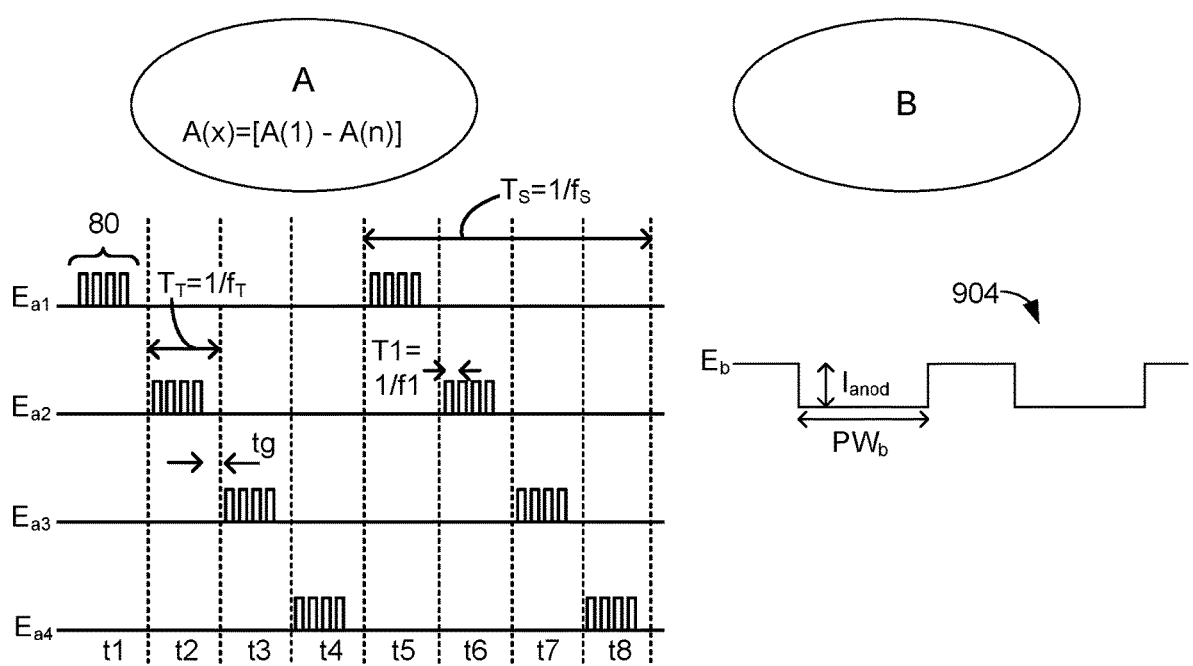
FIG. 9 shows an example of applying coordinated reset (CR) stimulation to one neural target and suppressing neuromodulation to a second neural target.

FIG. 9 illustrates an embodiment wherein a plurality of electrodes Ea1-Ea4 are placed in a region of neural anatomy with contains a majority of type A neurons and an electrode Eb is placed in a region containing a majority of type B neurons. Assume that the A region comprises n neural subpopulations A(x), denoted A(1)-A(n). The electrodes Ea1-Ea4 can be configured to provide coordinated reset stimulation to the population of A neurons. Coordinated reset involves using stimulation pulses at two or more electrodes Ex to stimulate different sub-populations of neurons within the target neural population A at different times. For example, a first packet of pulses 80 is issued from electrode Ea1 during a time period t1, with the goal of causing neurons within a first subpopulation A(1) within the neural target A to fire. Another packet of pulses 80 is issued from electrode Ea2 during a later time period t2, with the goal of causing neural elements (e.g., neurons, fibers, nerve terminals, etc.) within a second sub-population A(2) to fire, and so on for electrodes E3 and E4 and sub-populations A(3) and A(4) during times t3 and t4. The pulse packets 80 can then be repeated at electrodes Ea1-Ea4 during times periods t5-t8 as shown in FIG. 9. A gap in time tg may exist between successive pulse packets 80. According to some embodiments, the pulse packets 80 delivered to electrodes Ea1-Ea4 occur during a time period Ts, which preferably matches the frequency fs at which the sub-populations A(x) are noticed to oscillate, such as between 12 to 25 Hz for example.

Coordinated reset as provided by the pulse packets 80 of FIG. 9 may cause the phase of the oscillatory neural activity in the sub-populations A(x) to be altered. For example, assume that the time period between pulse packets, TT, may be 12.5 msec. Suppose that when sub-population A(1) fires, sub-population A(2) will naturally fire due to high entrainment 15 msec later when no further stimulation is present. Because the pulse packet 80 at electrode E2 is issued earlier than this—at 12.5 msec—the natural coupling between sub-populations A(1) and A(2) is disrupted. In other words, issuing the pulse packets 80 during time periods t1, t2, t3, etc., is likely to disrupt the otherwise naturally high coupling and phase of firing between the sub-populations A(x) were stimulation not used, which promotes desynchronization and assists in the reduction of symptoms. Thus, the coordinated reset stimulation excites the neural elements in the A population in a manner that suppresses their abnormal synchrony. In the embodiment illustrated in FIG. 9, electrode Eb is placed in a region containing a majority of type B neurons and configured to deliver a pulse train 904 that suppresses the activity of the B neurons.

As mentioned above, the GPe and STN form a reciprocally connected network that is implicated in pathological oscillations in PD. Thus, therapy targeting the denser PV-GPe neurons in the lateral GPe for coordinated reset stimulation may be used to treat or prevent such pathological oscillations. Thus, referring to FIG. 9, the neural population A may be the PV-GPe neurons in the lateral GPe and the neural population B may be the Lhx6-GPe neurons located in the medial GPe.

It should be noted that one example of coordinated reset stimulation has been described here. However, other coordinated reset stimulation methodologies can be used in embodiments of the present disclosure. For example, coordinated reset is described in co-owned U.S. Patent Publication 2018/0345022, the contents of which are incorporated herein by reference.

Figure 10:
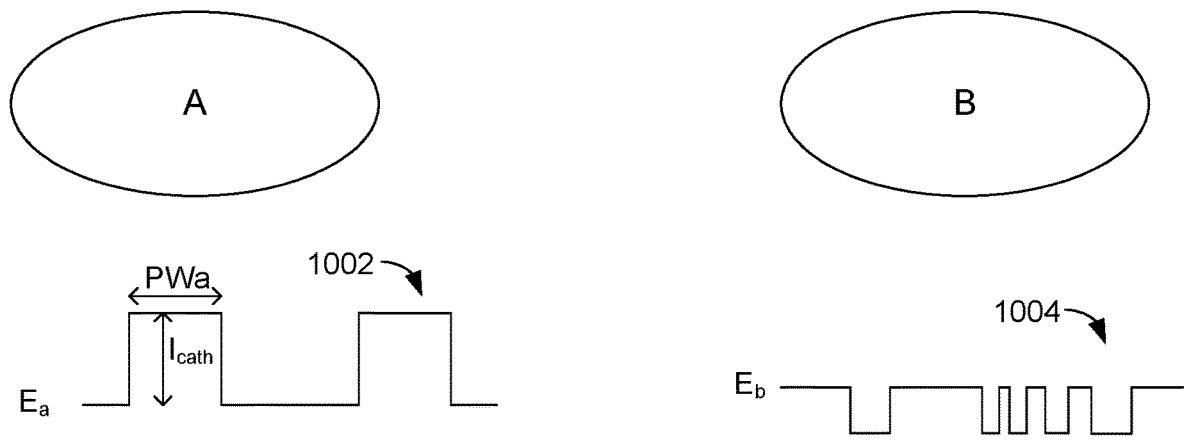
FIG. 10 shows an example of applying a regular neuromodulation waveform to a first neural target and applying a randomized neuromodulation waveform to a second neural target.

Referring again to FIG. 6-8, it should be mentioned that in some cases the natural (healthy) firing pattern of one of the neural elements (e.g., population A) may be regular, whereas the natural firing pattern of the other neural elements (e.g., population B) may be irregular. In such cases, the pulse train used to activate A may be regular and the pulse train (i.e., the anodic pulse train) used to inactivate B may be irregular. For example, as illustrated in FIG. 10, the cathodic pulse train 1002 applied at the population A is regular. However, the anodic pulse train 1004 applied at population B is irregular. For example, one or more parameters (i.e., frequency, pulse width, amplitude, etc.) of the waveform 1004 may be randomized. In the converse case, one may choose irregular patterns to activate A and regular (anodic) patterns to suppress activity of B.

Figure 11:
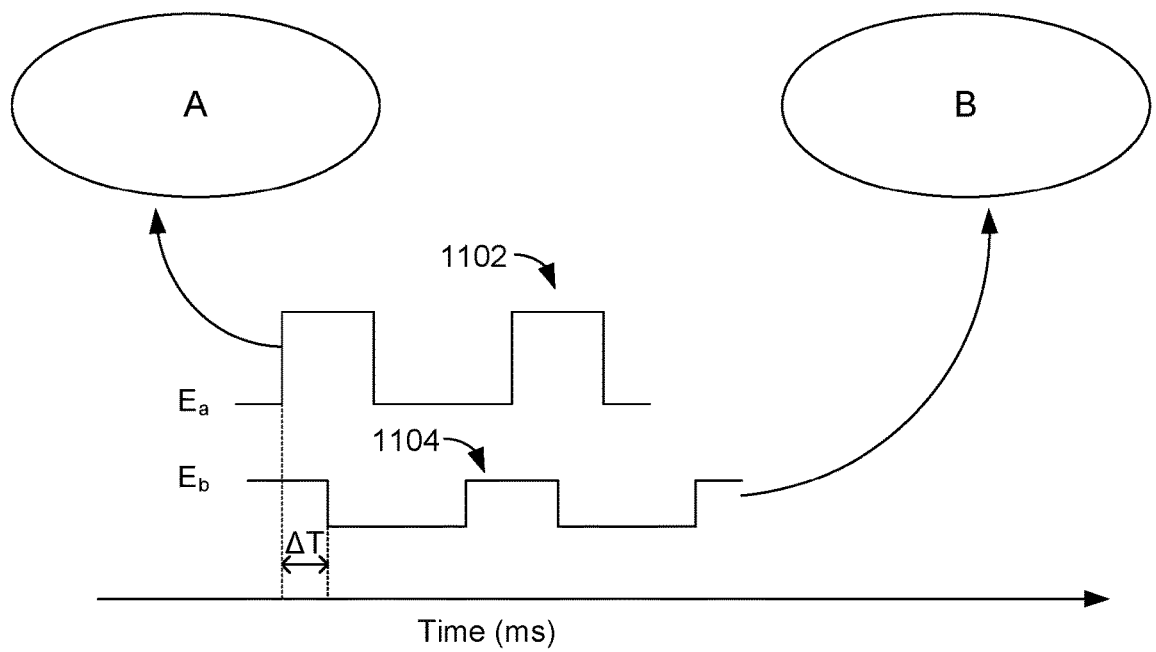
FIG. 11 shows an example of applying a first neuromodulation waveform to a first neural target and applying a second, delayed, neuromodulation waveform to a second neural target.

According to some embodiments, the timing of the pulse trains applied to the different neural populations A and B may be adjusted to account for differences in the timing at which the target neural populations fire. For example, referring to FIG. 11, assume that neural elements in population A are active Δ milliseconds before neural elements in population B. The pulse trains 1102 and 1104 delivered to A and B can be arranged so that the stimulating pulses delivered to population A by the electrode(s) Ea occur Δ milliseconds before the suppressing anodic pulses delivered to population B by the electrode(s) Eb. It should be noted that FIG. 11 illustrates an embodiment wherein populations A and B are modulated directly by the application of the pulse trains 1102 and 1104. However, the same methodology of adjusting the timing of the pulse trains can be applied to situations wherein the neural populations are modulated indirectly by applying the pulse trains to neural populations that project to A and B or that are projected to by A and B, as illustrated in FIGS. 7 and 8, respectively.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of providing electrical stimulation to a patient's brain using one or more electrode leads implantable in the patient's brain, wherein each electrode lead comprises a plurality of electrodes, the method comprising:
   identifying a first neural target for excitation in the brain,
   identifying a second neural target for suppression in the brain,
   based on the first identified neural target, using a first one or more of the electrodes to issue a first stimulation waveform to the first neural target, wherein the first stimulation waveform comprises one or more pulses having a first polarity, and
   based on the second identified neural target, using a second one or more electrodes to issue a second stimulation waveform to the second neural target, wherein the second stimulation waveform comprises one or more pulses having a second polarity opposite of the first polarity.

2. The method of claim 1, wherein the first stimulation waveform is configured to excite the first neural target.

3. The method of claim 1, wherein the second stimulation waveform is configured to suppress activity of the second neural target.

4. The method of claim 1, wherein the both the first and second stimulation waveforms are monophasic waveforms.

5. The method of claim 4, wherein the first stimulation waveform comprises first pulses having a first amplitude and a first pulse width, and wherein second stimulation waveform comprises second pulses having a second amplitude and a second pulse width.

6. The method of claim 5, wherein the first amplitudes and first pulse widths are each different in magnitude than the second amplitudes and pulse widths.

7. The method of claim 6, wherein charge transferred during each of the first pulses is essentially equal in magnitude to charge transferred during each of the second pulses.

8. The method of claim 1, wherein the first neural target is a first population of neural elements and the second neural target is a second population of neural elements different that the first population of neural elements.

9. The method of claim 8, wherein the first population of neural elements comprises projections to a third population of neural elements and wherein the first stimulation waveform is configured to modulate activity of the third population of neural elements.

10. The method of claim 9, wherein the first population of neural elements comprises neural elements of the PV-GPe and wherein the third population of neural elements comprises neural elements of the striatum and/or the parafascicular nucleus of the thalamus (pf).

11. The method of claim 10, wherein the first stimulation waveform is configured to treat pathological oscillations.

12. The method of claim 10, wherein the first stimulation waveform is configured to treat tremors.

13. The method of claim 8, wherein the second population of neural elements comprises projections to a fourth population of neural elements and wherein the second stimulation waveform is configured to modulate activity of the fourth population of neural elements.

14. The method of claim 13, wherein the second population of neural elements comprises neural elements of the Lhx6-GPe and wherein the fourth population of neural elements comprises neural elements of the striatum and/or the substantia nigra compacta (SNc).

15. The method of claim 14, wherein the second stimulation waveform is configured to modulate dopamine release from the SNc.

16. The method of claim 14, wherein the second stimulation waveform is configured to modulate motor output.

* * * * *